United States Patent [19]

Rule et al.

[11] Patent Number: 4,792,642

[45] Date of Patent: Dec. 20, 1988

[54] PROCESS FOR PREPARING IODINATED AROMATIC COMPOUNDS

[75] Inventors: Mark Rule; Gerald C. Tustin; Donald L. Carver; Jerry S. Fauver, all of Kingsport, Tenn.

[73] Assignee: Eastman Kodak Company, Rochester, N.Y.

[21] Appl. No.: 29,898

[22] Filed: Mar. 25, 1987

[51] Int. Cl.$^4$ .................... C07C 17/15; C07C 21/24
[52] U.S. Cl. .................................. 570/203; 570/204; 570/206
[58] Field of Search ............... 570/203, 206, 208, 204

[56] References Cited

U.S. PATENT DOCUMENTS

| | | | |
|---|---|---|---|
| 3,214,482 | 10/1965 | Caropreso et al. | 570/206 |
| 3,336,010 | 1/1968 | Schwarzenbek | 570/203 |
| 4,513,092 | 4/1985 | Chu et al. | 502/77 |

FOREIGN PATENT DOCUMENTS

| | | | |
|---|---|---|---|
| 0181790 | 5/1986 | European Pat. Off. | 570/203 |
| 183579 | 6/1986 | European Pat. Off. | 570/203 |
| 0077631 | 5/1982 | Japan | 570/206 |

OTHER PUBLICATIONS

Advanced Organic Chemistry; Reactions, Mechanisms, and Structure, Mar., McGraw-Hill, 1968, p. 405.

J. Org. Chem., vol. 35, No. 10, 1970, Baird et al., Halogenation with Copper (II) Halides, The Synthesis of Aryl Iodides.

Institute of Catalysis, Siberian Branch of the Academy of Sciences of the USSR, vol. 23, No. 4, pp. 992–994, Jul.-Aug., 1982; Gorodetskaya et al., Oxidative Bromination of Aromatic Compounds.

Chemical Economy & Engineering Review, Apr. 1984, vol. 16, No. 4 (No. 177) Itatani: International Technological Trends in $C_1$ Chemistry.

*Primary Examiner*—Werren B. Lone
*Attorney, Agent, or Firm*—Charles R. Martin; William P. Heath, Jr.

[57] ABSTRACT

Disclosed is a process for iodinating aromatic compounds by reacting an aromatic compound with oxygen at low temperatures in the presence of a non-acid catalyst containing an oxidation catalyst.

14 Claims, No Drawings

PROCESS FOR PREPARING IODINATED AROMATIC COMPOUNDS

BACKGROUND OF THE INVENTION

Field of the Invention

The present invention relates to processes for iodinating aromatic compounds over non-acid catalysts wherein the activity of the catalysts at low temperatures is enhanced by the Presence of an oxidation catalyst.

Discussion of Background

It has long been desired to be able to derivatize aromatic compounds and in particular condensed ring aromatic compounds in commercially attractive quantities since many of these compounds possess properties which would fill long sought needs. In particular, the compound 2 6-naphthalene dicarboxylic acid or its esters is particularly desired for use in the manufacture of polyesters which would have excellent barrier properties when fabricated into films bottles or coatinqs. However, known technigues for producing 2,6-naphthalene dicarboxylic acid and esters are very expensive and impractical for commercial exploitation.

Description of the Prior Art

Synthesis of iodobenzene starting from benzene and iodine is usually carried out in the liquid phase in the presence of an oxidative agent, preferably nitric acid. Such techniques have been described in the literature and in particular in Japanese No. 58/77830, U.S.S.R. Patent No. 463392 and by Datta and Chatterjee in the *Journal of the American Chemical Society*, 39, 437, (1917). Other oxidative agents have also been suggested but none of these have proven to be more efficient or convenient than nitric acid. Typical of the other oxidative agents which have been suggested are iodic acid, sulfur trioxide and hydrogen peroxide as described by Butler in the *Journal of Chemical Education*, 48, 508, (1971). The use of metal halogenides to catalyze iodination has been suggested by Uemura, Noe, and Okano in the *Bulletin of Chemical Society of Japan* 47, 147, (1974). The concept of direct iodination of benzene in the gas phase over the zeolite 13X has been suggested in Japanese patent publication 82/77631 in the absence of any oxidizing agent.

Ishida and Chono in Japanese Kokai No. 59/219241 have suggested a technigue for oxyiodinating benzene over very acidic zeolite catalysts having a silica to alumina ($SiO_2:Al_2O_3$) ratio of greater than 10. In this technique benzene is reacted with iodine in the presence of oxygen to produce iodinated benzene. According to this disclosure approximately 96% of the benzene which is converted is converted to iodinated form. However, the remaining benzene is oxidized to carbon dioxide and other combustion products resulting in the loss of valuable starting material.

Paparatto and Saetti disclosed in European Patent applications Nos. 181,790 and 183 579 techniques for oxyiodination of benzene over zeolite catalysts. European patent application No. 181,790 suggests the use of ZSM-5 and ZSM-11 type zeolites which has been exchanged prior to use with the least one bivalent or trivalent cation. According to this disclosure the utilization of these zeolites in the acid or alkaline form results in a rapid decrease in catalytic activity in relatively few hours.

European patent application No. 183,579 suggests the utilization of X type of Y type of zeolite in nonacid form. According to No. 183,579 the X or Y zeolites have to be used in the form exchanged with monovalent bivalent or trivalent cations and in particular with alkaline or rare earth cations. The techniques of Nos. 181,790 and 183,579 prepare the monoiodobenzene in selectivities in excess of 90% and only distinctly minor amounts of the diiodobenzene compounds.

Accordingly a need exists for a Process which can iodinate benzene at high conversions with substantially no oxidation of the benzene ring.

Further need exists for a process which selectively produces para-diiodobenzene with substantially no oxidation of the benzene ring.

Another need exists for a process which iodinates naphthalene preferentially at the 2-position with minimum formation of oxidation products.

A further need exists for a process which selectively produces 2,6-diiodonaphthalene with minimal oxidation of the naphthalene starting material.

Related Applications

Copending applications Ser. Nos. 912,806, filed Sept. 29, 1986 and 029,959 filed Mar. 25, 1987 disclose techniques for iodinating aromatic compounds over non-acid catalysts. The selectivities of these technigues to the desired products are improved by conducting the techniques at comparatively low temperatures on the order of from about 100° C.–250° C. However, the activity of the catalysts is substantially reduced at these low temperatures as compared with the activity obtained at higher temperatures.

Accordingly, a need exists for a technique which optimizes both selectivity and catalyst activity.

BRIEF DESCRIPTION OF THE INVENTION

Accordingly, one object of the present invention comprises a technique for increasing the catalytic activity of zeolite catalysts utilized in the iodination of benzene.

Another object of the present invention comprise the technique for increasing the activity of catalysts containing non-acidic sites utilized in the iodination of benzene.

Yet another object comprises a process for the selective iodination of benzene to para-diiodobenzene over a zeolite catalyst at hiqh catalytic activity.

Yet a further object of the present invention comprises the technique of the iodination of naphthalene in the 2-position over a zeolite catalyst at high catalytic activity.

A further object of the present invention comprises a process for the selective iodination of naphthalene to 2,6-diiodonaphthalene over a zeolite catalyst at high activity.

Yet a further object of the present invention comprises a technigue for the iodination of naphthalene in the 2-position over a catalyst containing non-acidic sites at high catalytic activity.

These and further objects of the present invention which will become apparent from the following disclosure have been attained by a process which comprises reacting an aromatic compound over an nonacid catalyst with a source of iodine and a source of molecular oxygen wherein the catalyst additionally contains an oxidation catalyst.

DESCRIPTION OF THE PREFERRED EMBODIMENTS

The aromatic compounds which can be utilized in practice of the present invention are esentially any aromatic compound including substituted and unsubstituted aromatics. Suitable aromatic compounds include hydrocarbon aromatics, nitroqen containing aromatics and sulfur containing aromatics. Typical hydrocarbon aromatics include benzene and biphenyl, condensed ring aromatics such as naphthalene and anthracene, sulfur containing aromatics including thiophene and benzothiophene nitrogen containing aromatics such as pyridine and benzopyridine and substituted aromatics such as sulfones, diaryl ethers, diaryl carbonyls, diaryl sulfides and the like. Aromatic compounds substituted by alkyl groups are generally not preferred for utilization in the present technigue. It has been found that alkyl substituted aromatics are iodinated not only on the ring but also on the side chains. Further, the product obtained will also contain oxidized side chains and the like. Thus, while alkyl substituted aromatics can be utilized in the present technique their use is not preferred.

The catalyst which may be employed in the present technique are described in copendinq applications Ser. Nos. 912,806, filed Sept. 29, 1986 and 029,959 filed Mar. 25, 1987. The disclosure of these applications incorporated herein by reference for more complete description of the catalyst in reaction conditions which are to be emPloyed.

The catalysts utilized in the present technique are generally characterized by containing non-acid sites, and more preferably basic sites. Non-zeolite catalysts generally do not exhibit the selectivity of the zeolite catalyst when producing polyiodinated products. Thus, when it is desired to produce para-diiodobenzene or 2,6-diiodonaphthalene it is preferred to employ a zeolite catalyst because of their greater selectivity.

The type of zeolite which is utilized is not critical so long as greater than 10% of exchange cations are alkali alkaline earth or rare earth metals and the pore size is qreater than about 6 Å. In general, the reaction rate is a function of silicon to aluminum ratio in the zeolite, since aluminum is part of the active site. It is preferred to use zeolites with a silicon (as Si) to aluminum (as Al) ratio of 10:1 or less, more particularly 5:1 or less, still more preferred are those zeolites having a silicon to aluminum ratio of 3:1 or less with the most preferred tyPe having a silicon to aluminum ratio of 1.5 or less. Particular types of zeolites which have proven to be particularly effective are the X and Y types. The Y type zeolite generally has a silicon to aluminum ratio of about 1.5 to 1 to 3:1. The X type zeolite is generally considered to have a silicon to aluminum ratio of 1:1 to 1.5:1.

Most of the commerically available zeolites contain mainly sodium counter ions. However, alkali, alkaline earth and rare earth metal counter ion containing zeolites have all proven to be useful for the iodination of benzene. The alkali or alkaline earth metals containing zeolites are preferred because there is substantially no oxidation or burning of the benzene when these are used as the counter ions. The zeolites which have been ion exchanged with the rare earth metals show a higher burn rate which is generally not desired.

The counter ion is easily introduced into the zeolite by simple ion exchange and is well known to those skilled in the art. This is generally accomplished by contacting in an agueous medium a salt of desired counter ion and the zeolite. The period of time over which the contact is conducted and a number of times the ion exchange process is performed is dependent upon the degree of replacement which is desired. Thus, one beginning with the zeolite in the sodium form may ion exchange this material with another counter ion to partially or substantially completely replace the sodium ion with a different counter ion.

The particular counter ion which is employed has an effect upon the product composition. The X type zeolite exhibits more sensitivity to the counter ion than the Y type does. That is, the selectivity of the X type zeolite to the production of specific mono, di or tri iodinated aromatic compounds can be altered more successfully with the selection of the appropriate counter ions than can the Y type. While not being bound to any particular theory it is believed that the counter ion affects the selectivity by altering the shape of the pore thereby increasing or decreasing the selectivity of the catalyst for any particular isomer as compared with the standard sodium form. As a number of cations at the exchange site decreases the effect of counter ions on the shape of the pore decreases and thus selectivity decreases. Thus, when one desires to produce a particular isomer high alumina content zeolites are preferred.

When the aromatic compound is a condensed ring aromatic such as naphthalene, it is preferred that the zeolite has been ion exchanged with sodium, potassium, rubidium and/or cesium and more preferably with potassium, rubidium or cesium. It has been found that when the zeolite is ion exchanged with lithium, calcium, strontium, barium or rare earth metals the condensed ring aromatics are oxidized by the oxygen present in the gas stream to a high degree at temperatures of 250° C. or above. It was surprising to discover that with potassium rubidium and cesium the degree of naphthalene oxidation is significantly less than 1% of the naphthalene converted. That is, essentially no oxidation of naphthalene occurs with these counter ions. When the zeolite is essentially in the sodium form, oxidation of the naphthalene occurs but to a lesser extent than with lithium, calcium, strontium, barium and rare earth metal counter ions. In view of the higher oxidation rate obtained when the zeolite is in the sodium form, it is preferred that the zeolite be ion exchange with potassium, rubidium and/or cesium such that at least 50% of the sodium ions are replaced by one or more of potassium, rubidium or cesium.

When one desires to produce the 2,6-diiodonaphthalene compound the 13 X type zeolite is preferred. The most preferred zeolite to produce the 2,6-diiodonaphthalene is the 13 X type which has been ion exchanged with potassium, rubidium or cesium. The ratio of 2.6- to 2.7-diiodonaphthalene qenerally increases with increasing amounts of these ions. The preferred counter ions for the production of p-diiodobenzene are sodium, potassium, rubidium and cesium and barium. From a cost standpoint, potassium is the most preferred counter ion for the production of p-diiodobenzene although rubidium and cesium are equally effective.

Typical non-zeolite catalysts are alkali or alkaline earth cations on inert supports. Suitable supports include alumina, silica, silica-alumina, titania, etc. The alkali or alkaline earth cations can be supported by any suitable technique, such as impregnation from aqueous solution.

These catalysts may be supported or unsupported or bound together with a binder to form a shaped particle. Typical supports and binders include silica, alumina, various clays and the like. In general, any material not containing acid sites can be utilized as the support. It is also possible to utilize the catalyst in powder form, especially when the reaction is to be conducted in a fluidized bed or in the liguid phase wherein the catalyst would be suspended in the liquid reactant.

In general, the catalyst selectivity increases with decreasing reaction temperature; however, catalyst activity also decreases with decreasing temperature. In order to increase the catalytic activity at low temperatures, it is desirable to incorporate in the catalyst an oxidation catalyst in an amount sufficient to increase the reaction rate. As oxidation catalyst one may use essentially any metal having a variable valence. The metals may be added in the form of an oxide, salt or acid form and achieve the desired results. Suitable oxidation catalyst include manganese, iron, copper. chromium, vanadium, arsenic, antimony, cobalt, boron and molybdenum. The form in which these materials are added to the reactor is not critical and may be added in the form of oxides, salts, acids and the like. Examples of catalysts include manganese chloride iron sulphate, potassium molybdate, boric acid, cobalt chloride and the like.

The amount of oxidation catalyst to be incorporated with the iodination catalyst is chosen so as to effectively increase the activity of the iodination catalyst. Generally, the amount of oxidation catalyst necessary is less than 1% by weight of the iodination catalyst although greater quantities may be used if desired. The utilization of oxidation catalyst in excess of 1% does not offer any increased activity over the utilization of lesser amounts. The use of great excesses of oxidation catalyst should be avoided since these catalysts occupy some of the active sites on the iodination catalyst and if used in greater excesses can actually reduce the catalyst activity by eliminating active sites. The preferred quantity of oxidation catalyst which is employed is less than 1% by weight of the iodination catalyst and more preferably less than 0.5 wt. %. The minimum amount of oxidation catalyst employed is that necessary to increase the catalytic activity of the iodination catalyst at the reaction temperature of interest. In general, the higher the reaction temperature the lower the quantity of oxidation catalyst which is necessary.

Without being bound by any particular theory, it is believed that the oxidation catalyst facilitates the reactivation of the basic catalyst by the oxygen. During the iodination reaction ½ mole of iodine becomes associated with the active site on the iodination catalyst and ½ mole is utilized to iodinate the aromatic compounds. The oxygen reactivates the catalyst by releasing the iodine which is then free to react with additional aromatic comPuunds.

The temperature which the reaction is to be conducted is not critical and can be any temperature which when the aromatic compound is fluid. The maximum temperature at which the process can be carried out is that at which combustion of the aromatic compound occurs. Generally, temperatures of from about 100° to 500° C. have been found satisfactory, with temperatures of from 200° to 400° C. being preferred. preferably from about 20° to 250° C. When operating at the lower ranges, the oxidation catalyst have their greatest effect in increasing the activity of the iodination catalyst. Surprisingly, the presence of the oxidation metals do not significantly increase the degree of combustion of the aromatic compounds. This is especially unexpected for naphthalene, since these same oxidation metals are utilized in processes for the partial combustion of naphthalene.

The pressure which the process is conducted is not critical and can range from subatmospheric to superatmospheric. The utilization of elevated pressures in the gas phase process may be preferred so as to minimize eguipment size. In general, pressures from atmospheric to 600 psig have proven satisfactory although higher or lower pressures can be utilized.

The molecular oxygen can be introduced as pure oxygen, air or oxygen diluted with any other inert material such as carbon dioxide or water vapor. Essentially oxygen from any convenient source may be utilized. The purpose of the oxygen is to regenerate the active site on the zeolite to its active form once the iodination reaction has occurred. Thus, the amount of oxygen present during the reaction is not critical. However it is preferred that at least ½ mole of oxygen be used for every mole of iodine. The molar ratio of iodine to benzene which is to be reacted is largely determined by whether one desires to produce a monoiodinated aromatic product or polyiodinated aromatic product. Stoichiometrically, ½ mole of iodine reacts with 1 mole of aromatic compound to produce the monoiodated form. Similarly on a stoichiometric basis 1 mole of iodine is required to convert 1 mole of aromatic compound to tbe diiodinated form. Greater or lesser quantities of iodine can be utilized as the artisan may desired. The utilization of excess quantities of iodine result in the product which is contaminated with unreacted iodine and thus will contain a high color level. In general, it is desired to run the process to obtain as close to 100% conversion of the iodine as practical so as to simplify the purification steps in the recovery of any unreacted iodine. Suggested mole ratios of aromatic compound to iodine to oxygen are from 1:0.05:0.025 to about 1:2:3. However other ratios may be utilized as desired.

Essentially any source of iodine may be employed includinq elemental iodine, $I_2$, hydroiodic acid in a qaseous form or alkyl iodines, preferably lower alkyl iodines. Furthermore, mixtures of these materials may be used as the source of iodine.

It is anticipated by the present process would be carried out continuously by the continuous addition of iodine, oxygen and aromatic compound to the reactor, however, the process can be carried out as a batch or semibatch processe if desired. Further, the aromatic compound and iodine can be reacted over the catalyst to produce the iodinated product, the addition of the aromatic compound and iodine then being terminated and oxygen then added to the reactor to regenerate the catalyst to its active form and then the process commenced again. Alternatively, in a continuous process it is possible to utilize two reactants circulating the catalyst between them. In the first reactor the iodine and aromatic compound would be added and reacted to form the iodinated compound. The catalyst would then be circulated to the second reactor where it would be contacted with oxygen to be regenerated and then recycled to the first reactor to catalyze additional reactions of aromatic compound with iodine.

The space velocity of the process is not critical and may be readily selected by the artisan. In vapor phase operation, gas hourly space velocities between 10 and 50,000. Preferably between 100 and 20,000 liters per hour of reagents per liter of active zeolite, have proven satisfactory.

The catalyst is proven to have an extremely long life and degrade only slowly with time. The degradation of the catalyst is believed to be caused by the combustion of very small quantities of the aromatic compound which deposits small quantities of carbon on the active sites thereby degrading the catalyst activity. When the reaction conditions are selected such that none of the aromatic starting material is oxidized, the life of the catalyst is essentially indefinite. However, when the catalyst becomes deactivated reactivation is simple. An excellent regeneration technigue comprises passing air or oxygen over the catalyst for several hours at elevated temperatures. Typically the temperature is above 400° C. althouqh higher or lower temperatures are proven equally satisfactory. The temperature need only be high enough so as to ensure combustion of the carbon deposit on the catalyst. When pure oxygen is employed lower temperatures can be utilized, while when air is employed temperatures on the order of about 400° C. have proven satisfactory.

The following examples are presented to illustrate the present invention but are not intended in any way limit the scope of the invention which is defined by the appended claims.

denum, arsenic, antimony, cobalt and boron in the oxide, salt or acid form.

2. The process of claim 1 wherein said zeolite contains less than about 1 wt % for said oxidation catalyst.

3. The process of claim 1 wherein said zeolite contains less than about 0.5 wt % of said oxidation catalyst.

4. The process of claim 1 wherein said zeolite is the 13X type which has been ion exchanged with at least one of potassium, rubidium or cesiuim.

5. The process of claim 1 wherein said aromatic compound is benzene.

6. The process of claim 1 wherein said aromatic compound is napthalene.

7. The process of claim 1 wherein the reaction temperature is from about 200° C. to about 400° C.

8. The process of claim 1 wherein the reaction temperature is from about 200° C. to about 250° C.

9. A process for mono- or di-iodinating an aromatic compound selected from the group consisting of benzene, biphenyl, naphthalene, anthracene, thiophene, benzothiophene, pyridine and benzopyridine which comprises reacting an iodine source with said aromatic compound in the presence of oxygen over a non-acid catalyst selected from the group consisting of alkali or alkaline earth cations on an inert support at a temperature between about 100° C. to about 500° C., wherein

| Ex. No. | Temp. °C. | $C_{10}H_8$ mmol min$^{-1}$ | $I_2$ mmol min$^{-1}$ | $O_2$ mmol min$^{-1}$ | Catalyst (50 cc) | Products (mole %) | | | Wt. % $I_2$ | Vent Gas % $CO_2$ | 2,6/2,7 |
|---|---|---|---|---|---|---|---|---|---|---|---|
| | | | | | | $C_{10}H_8$ | $C_{10}H_7I$ | $C_{10}H_6I_2$ | | | |
| 1 | 225 | 3.0 | 1.5 | 3.0 | K-X | 78.4 | 17.4 | 4.1 | 63.7 | 0.03 | 8.7 |
| 2 | 250 | 3.0 | 1.5 | 3.0 | K-X | 58.9 | 29.0 | 12.2 | 23.3 | 0.04 | 4.5 |
| 3 | 300 | 3.0 | 1.5 | 3.0 | K-X | 10.1 | 45.3 | 36.1 | 1.2 | 0.2 | 2.2 |
| 4 | 200 | 3.0 | 1.5 | 3.0 | 1% $V_2O_5$—KX | 52.9 | 32.1 | 13.0 | 35.5 | 0.03 | — |
| 5 | 220 | 3.0 | 1.5 | 3.0 | 1% $V_2O_5$—KX | 34.6 | 46.0 | 17.0 | 23.8 | 0.036 | — |
| 6 | 250 | 3.0 | 1.5 | 3.0 | 1% $V_2O_5$—KX | 27.7 | 52.9 | 19.3 | 8.4 | 0.11 | 4.0 |
| 7 | 300 | 3.0 | 1.5 | 3.0 | 1% $V_2O_5$—KX | 9.7 | 43.6 | 37.1 | 0.8 | 0.45 | — |
| 8 | 250 | 3.0 | 1.5 | 3.0 | NaX | 77.3 | 14.7 | 7.9 | 59.0 | 9.7 | — |
| 9 | 250 | 3.0 | 2.25 | 4.5 | 1% $FeSO_4$—KX | 3.1 | 42.9 | 42.0 | 8.1 | 0.16 | — |
| 10 | 250 | 3.0 | 2.25 | 4.5 | 1% $CrCl_3$—KX | 4.4 | 59.8 | 34.8 | 6.4 | 0.12 | — |
| 11 | 220 | 3.0 | 2.25 | 4.5 | 0.2% $CuCl_2$—KX | 4.0 | 28.1 | 53.3 | 6.1 | 0.15 | 4.7 |
| 12 | 250 | 3.0 | 2.25 | 4.5 | 0.5% $MoO_3$—KX | 6.0 | 35.4 | 43.2 | 11.3 | 0.09 | — |
| 13 | 225 | 3.0 | 1.5 | 3.0 | 10% KF—$Al_2O_3$ | 83.0 | 10.9 | 6.1 | 50.7 | 0.03 | |
| 14 | 225 | 3.0 | 1.5 | 3.0 | 10% KF—1% $FeSO_4$—$Al_2O_3$ | 65.4 | 25.3 | 9.3 | 42.4 | 0.03 | |

| Ex. No. | Temp. °C. | $C_6H_6$ mmol min$^{-1}$ | $I_2$ mmol min$^{-1}$ | $O_2$ mmol min$^{-1}$ | Catalyst (50 cc) | Products (mole %) | | | Wt. % $I_2$ | Vent Gas % $CO_2$ |
|---|---|---|---|---|---|---|---|---|---|---|
| | | | | | | $C_6H_6$ | $C_6H_5I$ | $C_6H_4I_2$ | | |
| 15 | 300 | 5.6 | 1.5 | 5.0 | K—X | 77.7 | 17.8 | 4.5 | 23.0 | 0.30 |
| 16 | 300 | 5.6 | 1.5 | 5.0 | 0.2% $CoCl_2$—KX | 66.7 | 21.4 | 11.6 | 7.8 | 0.35 |
| 17 | 300 | 5.6 | 1.5 | 5.0 | 0.3% $H_3BO_3$—KX | 65.2 | 21.5 | 13.3 | 4.7 | 0.38 |

While the invention has been described in detail with particular reference to preferred embodiments thereof, it will be understood that variations and modifications can be effected within the spirit and scope of the invention.

We claim:

1. A process for mono- or di-iodinating an aromatic compound selected from the group consisting of biphenyl, naphthalene, anthracene, thiophene, benzothiophene, pyridine and benzopyridine which comprises reacting an iodine source with said aromatic compound in the presence of oxygen over a non-acid zeolite catalyst at a temperature from about 100° C. to about 500° C. wherein said non-acid zeolite catalyst contains an effective amount of an oxidation catalyst comprising at least one member selected from the group consisting of manganese, iron, copper, chromium, vanadium, molybsaid non-acid catalyst contains an effective amount of an oxidataion catalyst comprising at least one member selected from the group consisting of manganese, iron, copper, chromium, vandium, molybdenum, arsenic, antimony, cobalt and boron in the oxdde, salt or acid form.

10. The process of claim 9 wherein said non-acid catalyst contains less than about 1 wt % of said oxidation catalyst.

11. The process of claim 9 wherein said non-acid catalyst contains less than about 0.5 wt % of said oxidation catlayst.

12. The process of claim 9 wherein said aromatic compound is benzene.

13. The process of claim 9 wherein said aromatic compound is napthalene.

14. The process of claim 9, wherein said inert support is selected from the group consisting of alumina, silica, silica-alumina and titania.

* * * * *